United States Patent [19]
Daub et al.

[11] Patent Number: 5,252,757
[45] Date of Patent: Oct. 12, 1993

[54] DICVANOAZULENYL AND DICYANOVINYL SUBSTITUTED FURAN

[75] Inventors: Jorg Daub, Regensburg; Knut M. Rapp, Offstein; Petra Seitz, Straubing; Rainer Wild, Obrigheim; Josef Salbeck, Regensburg, all of Fed. Rep. of Germany

[73] Assignee: Suddeutsche Zucker-Aktiengsellschaft, Mannheim, Fed. Rep. of Germany

[21] Appl. No.: 736,545

[22] Filed: Jul. 26, 1991

Related U.S. Application Data

[60] Division of Ser. No. 445,092, Dec. 5, 1989, Pat. No. 5,091,538, which is a continuation-in-part of Ser. No. 195,754, May 19, 1988.

[30] Foreign Application Priority Data

Jun. 5, 1987 [DE] Fed. Rep. of Germany ....... 3718917

[51] Int. Cl.$^5$ .................. C07D 307/14; C07D 307/42; C07D 307/54
[52] U.S. Cl. ..................................... 549/491; 549/214; 549/218; 549/472; 549/481; 549/497; 549/499; 549/502; 546/283
[58] Field of Search .......................................... 549/491

[56] References Cited
PUBLICATIONS

Chemical Abstracts, vol. 112 (No. 27) Abst. No. 54688-e Feb. 12, 1990.

Primary Examiner—Alan L. Rotman
Attorney, Agent, or Firm—Shea and Gould

[57] ABSTRACT

A cycloadduct of the formula

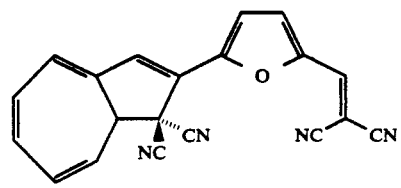

is prepared by reacting 2,2'-(2,5-furandiyldimethylidine)bis-propanedinitrile with 8-methoxyheptafulvene to form a tetrahydroazulene intermediate and then heating a solution of the tetrahydroazulene intermediate in a boiling solvent to drive off methanol.

2 Claims, 4 Drawing Sheets

DICYANOAZULENYL AND DICYANOVINYL SUBSTITUTED FURAN

This is a continuation of application Ser. No. 445,092 filed Dec. 5, 1989 and now U.S. Pat. No. 5,091,538, which is a continuation-in-part of 07/195,754 filed May 19, 1988, now abandoned.

Dicyanovinyl substituted furan derivatieves, process for obtaining them and their applications.

The present invention refers to novel furan derivatives according to the general formula I shown in claim 1, which as a result of their properties, are suited in a special way among others for electro-optical applications.

Compounds, which are capable of producing a dyestuff and therefore an image, by light-absorption, without any developing or washing processes, can be utilized in optical informational recording- or processing systems. Because it is possible with these substances to make grain-free layers, very great storage densities are reachable (Chemiker-Zeitung 96, 535 (1972)).

Spiropyranes as those like formula 1

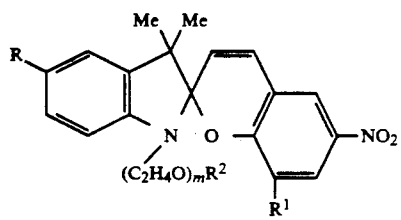

(comp. JP 61 18 782 (86 18 782); Chem Abstr. 105, 78 849 q (1986)) belong to substances, which can be changed by UV-exposure to colored compounds and which can be discolored by heat influence.

The applications and advantages of reversible photochromic substances are described in "Chemie in unserer Zeit" 9, 85 (1975), namely the high optical resolution (high storage density), the control of exposure during the "writing", and the possibility of erasure or changing of parts of a picture.

In Kirk-Othmer, Encyclopedia of chemical technology 3. Ed. Vol. 6, 122 (1979) are mentioned as disadvantages of organic photochromic materials: small spectral shifts, slow reversal times, fatigue, or any combination of the three.

As class of substances, where a valence tautomerism is responsible for the chromogenic behavior spiropyranes and fulgides are mentioned. The former can be partly built in a polymer by co-polymerization with a suitable monomer. Fulgide belong also to the more intensely studied photochromic systems (comp e.g. Chem Abstr. 102, 229 304z (1985), Gb 2 142 011 cited in Chem Abstr. 103, 79 543 f (1985) with compounds of formula 2).

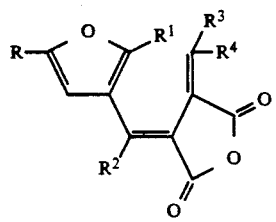

In Angew. Chem. 96, 980 (1984) a system is described, in which a dihydroazulene derivative via light absorption is transformed in a colored heptafulvene derivative which cyclizes by heat treatment again to the dihydroazulene. In contrast to $R=NO_2$ the system $3A \rightleftharpoons 3B$

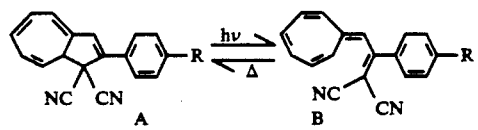

is chemically stable for $R=OCH_3$, i.e. an at least 15-fold fore- and backreaction doesn't change the extinction coefficient. No side reactions or irreversible degradation takes place.

Figure 1A:
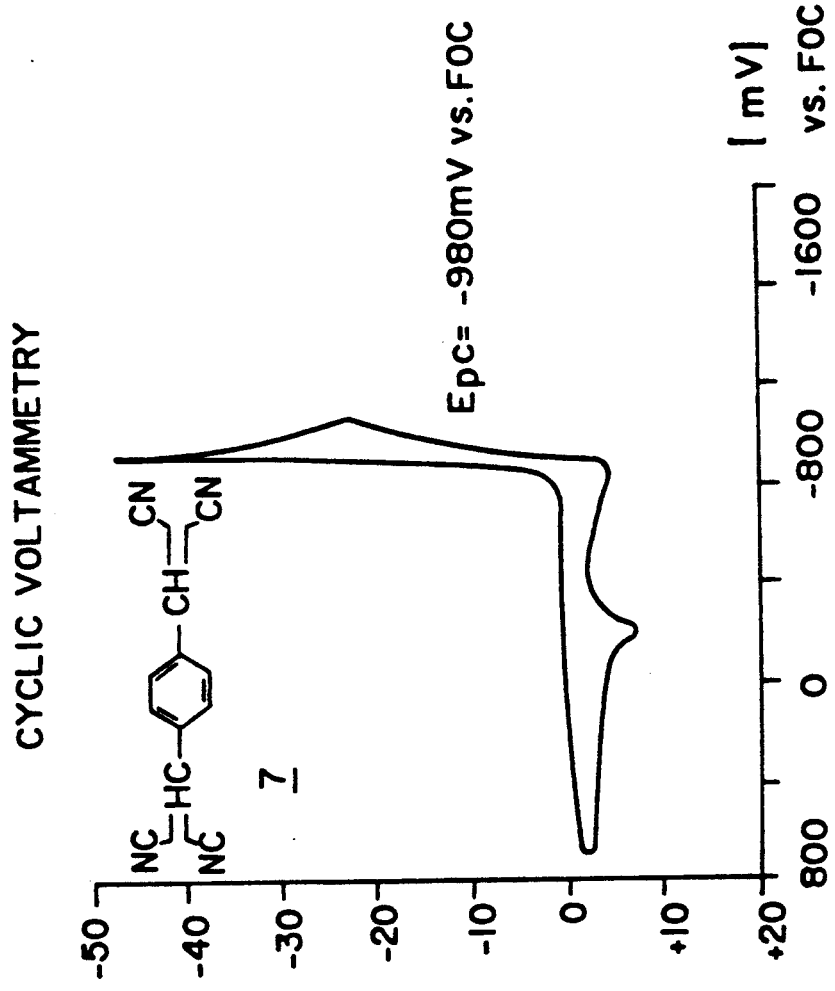
FIGS. 1A and 1B are graphs of the cyclic voltammetry of 2,2'-(2,5-furandiyldimethylidyne)-bis-propanedinitrile in acetonitrile and 0.1N tetrabutylammonium hexalfuorophosphate, respectively.

The above described photochromic system is synthesized according to the following reacting sequence:

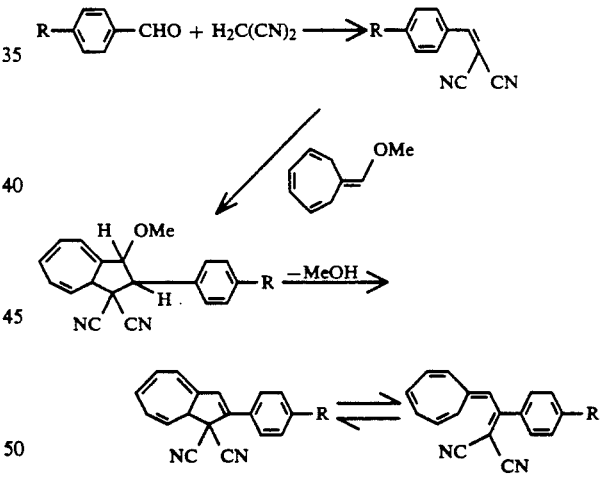

8-Methoxyheptafulvene is accessible in two steps and good yield starting from cyclooctatetraene. A disadvantage of the applied p-anisaldehyde ($R=OCH_3$) is the absence of a functional group, which would allow to connect the photochromic product in a suitable manner e.g. covalently to polymers.

Surprisingly advantageous however is the utilization of 5-hydroxymethylfurfuraldehyde (in the following called HMF) with formula 4 instead of

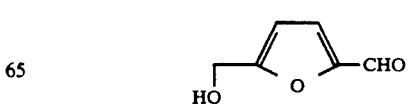

anisaldehyde for the following reasons:

1.) The electronic influence of a furan ring on bound substituents is comparable with this of an O-alkylbenzene ring, i.e., that furfuraldehyde reacts similarly as anisaldehyde (p-methoxybenzaldehyde).

2.) The hydroxymethyl group in HMF enables, as additional functional group, a coupling to an oligo- or polymer. Such a bonding is mentioned clearly as an advantage in the case of spiropyranes (Kirk-Othmer, Encyclopedia of chemical technology 3. Ed. Vol. 6, 122 (1979). A derivatization at the hydroxymethyl group allows also a systematic control of the solubility.

3.) Typical carbonyl reactions allow too, through a condensation with amines and a following oxidation of the hydroxymethyl group to the aldehydic state, to prepare e.g. compounds with formula 5,

which are obtained via Knoevenagel-reaction with malononitrile.

4.) The possibility to "build" different bridges between two furans, allows a perturbation of the dicyanovinyl groups and so a variation of the electron acceptor ability or of the di- or polyeneophilic properties.

5.) 5-Hydroxymethylfurfuraldehyde has as starting component additionally the great advantage to be prepared in a single reaction step from renewable raw material (carbohydrate) and moreover on large-scale with water as sole solvent. Especially, the utilization of agricultural, (occasionally) on surplus produced carbonhydrates e.g. sucrose, in technical fields via the intermediate HMF shows the advantage of the inventive dicyanovinylsubstituted furans.

6.) Another surprising advantage of furylidenemalononitriles compared with phenylanaloga is e.g. the full reversibility of the reduction of compound 6, as shown by cyclovoltammatry. Compound 7 is under the same conditions not reversibly reducible. This is also to see in connection with the substituent effect mentioned in 1.

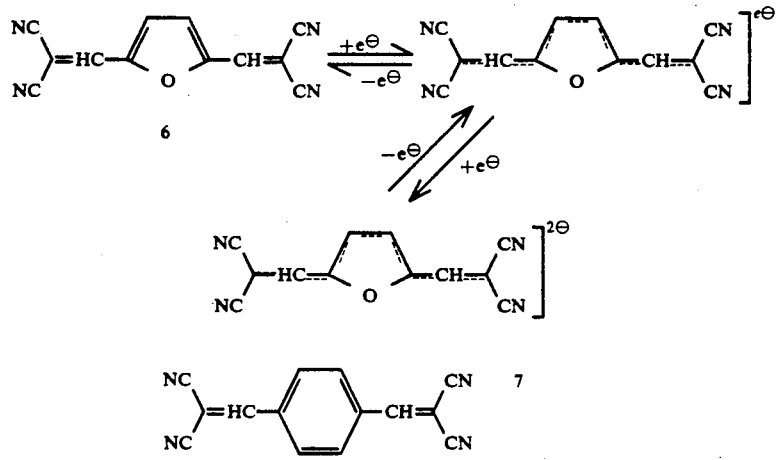

This means, that the compound 6 similar to tetracyanoquinodimethane (TCNQ) (formula 8)

which can be reversibly reduced also in a twofold one-electron reaction, can be used as component of so-called "organic metals", or an electron-storage system or electron-transfer-catalyst.

The spectroelectrochemistry of 6 shows reversible electrochromic behavior. An application in displays is possible because of the good reversibility of the electron absorption.

Details due to the reduction of 6, as determined by cyclovoltammetry under aprotic conditions under formation of 6·−, respectively 6²− as well as to the absorption spectrum of the radical anion and the dianion formed and obtained by spectroelectrochemistry are shown in FIGS. 1 and 2. Radical anion 6·− displays a rather narrow absorption band at $\lambda = 599$ nm (dark blue solution) with a high extinction coefficient. Thus, contrarily to the radical anion 8·− of TCNQ with an absorption at $\lambda = 840$ nm, radical anion 6·− absorbs in the visible part of the spectrum.

The reversible reducibility of alkylidene malononitriles is mentioned in Angew. Chem. 88, 311 (1976). The formation of radical anions of tetracyanoethylene or TCNQ is also described in Kirk-Othmer, Encyclopedia of chemical technology 3. Ed. Vol. 7, 359, 362 (1979).

A correlation between reversible redox properties (electrochemistry) and chromogenic features (photochemistry) appears too in the long-known class of fulgides. Thus, in J. Amer. Chem. Soc. 106, 7626 (1984) is described, that the reversible generated radical anion of formula 9 reacts in an electro-cyclic reaction to a structure similar to the ring-closed, photochemically produced of chromogenic fulgides.

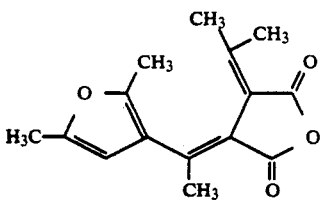

In Angew. Chem. 90, 927 (1978) tetracyano compounds are mentioned among others too, and applications of these two-step redox systems as redox indicators, electron acceptors, catalyst for electron transfer, light-sensitive systems and electron conducting materials are mentioned.

The furylidenmalononitriles described in this invention can therefore be characterized as important new substance class for electro-optical applications.

7.) An advantage of furanic substituents at the dihydroazulene residue is also the rapid back-reaction of the colored heptafulvene structure after light exposure, which is favored in addition to electron withdrawing substituents for A, e. g. $A = A^1 = CH = C(CN)_2$, $NO_2$. A slow back-reaction is mentioned in Kirk-Othmer, Encyclopidia of chemical technology 3. Ed. Vol. 6, 124 (1979), as an explicit disadvantage of organic photochronic materials.

For a fast optical information-storing and processing, furylidenmalononitrile-derivatives, analogous to 5, meet ideal preconditions.

8.) Another advantage of the dihydroazulene-heptafulvene-systems $3A \rightleftarrows 3B$ ($R = OCH_3$) is also the relatively great shift from about 380 nm to about 470 nm with a simultaneous increase of the extinction coefficient. Processes for producing 3- and/or 4-substituted HMF-derivatives are described e.g. in Carbohydr. Res. 155, 99 (1986), where via the oxidation of 1,2; 4,5-diisopropylidenfructose followed by a Grignard-reaction und dehydratisation several 3-substituted HMF-derivatives are synthesized e.g. formula 10

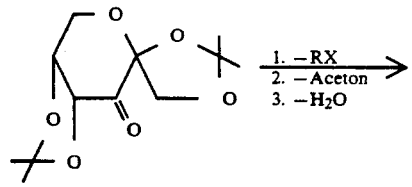

R = Me, Ph, $CH_2$—CH=$CH_2$

Other substituents can be introduced in the furan ring according to the rules of the chemistry of aromatic compounds. The 3- or 4-substituted HMF-derivatives are further reacted as the unsubstituted HMF.

The preparation of compounds with n=0 and $A = A_1 = CH_2OR^1$ is achieved by an etherification or esterification e.g. with acetic anhydride of HMF followed by a Knoevenagel-condensation.

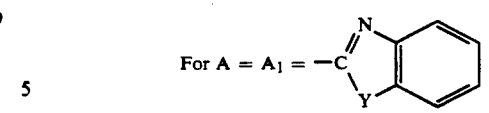

One starts from HMF and a suitable ortho-disubstituted phenyl derivative and makes first the aminal or O, N- or S, N-acetal, which is oxidized in one step e.g. with $BaMnO_4$ to the aromatic (e.g. Benzimidazol) and at the same time to the aldehydic stage (from the hydroxymethyl group).

The cross benzoin addition with HMF or derivatives thereof as e.g. 5-acetoxymethylfurfuraldehyde followed by oxidation leads to compounds e.g. of formula 11

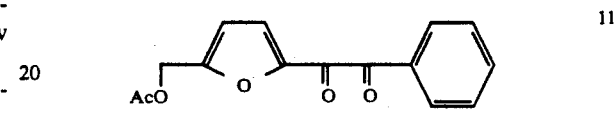

The oxidation of the deacetylated compound and Knoevenagel-condensation with malononitrile yields compounds according to formula

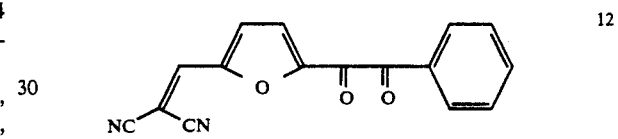

General manufacturing method for n=1 and $A = A_2$. =—CH=N—Z—N=CH—:

The diamino compound is dissolved in a suitable solvent optionally as hydrochloride or a similar salt, e.g. hydrazine hydrochloride or -hydrogenesulfate in water or ethylenediamine, 1,12-diaminododecane or p-phenylenediamine in methylene chloride. To the stirred solution two mol equivalents of HMF, is dropped slowly at room temperature dissolved in a suitable solvent, e. g. water or methylene chloride.

Either a solid precipitates in a short time, which is optionally recrystallized but also can be used often directly in the following oxidation step, or it has to be heated for the formation of the Schiff base and/or water removing agents had to be added. The conditions for the formation of Schiff bases are described e.g. in J. March, Advanced Organic Chemistry 3. Ed., 1985 J. Wiley & Sons, Inc., N.Y., S. 796–798.

The oxidation of the both hydroxymethyl groups in these amine-HMF-condensation products can be achieved e.g. with active manganese dioxide or barium manganate. In contrast to the literature, Synthesis 1976 133, where it is started that azines are unstable in the presence of manganese dioxide, the oxidation of the HMF-azine is possible. In the inventive process other oxidants (besides the mentioned manganese compounds), which are able to oxidize hydroxymethyl groups to the aldehydic stage, are not excluded. Thin layer chromatographically the oxidation progress can be followed. The oxidation can be made in benzene, toluene or trichloroethane eventually with concomitant azeotropic destillative removing of the reaction water.

The obtained dialdehydes are reacted with malononitrile according the common procedures, optionally with $TiCl_4$ catalysis, and the dicyanovinylsubstituted furan derivatives are received as good crystallizing solids.

Examples of compounds with n=0
A=A₁=CH₂OR¹:

R¹=H, methyl, ethyl, n-propyl, i-propyl, n-butyl, t-butyl, octyl, phenyl, p-hydroxyphenyl, p-nitrophenyl, p-dimethylaminophenyl, 2-pyridyl, 1-naphtyl, 2-naphtyl, trimethylsilyl, triphenylsilyl, acetyl, palmitoyl, benzoyl, p-nitrobenzoyl, p-dimethylaminobenzoyl, methansulfonyl, p-toluenesulfonyl, phosphonyl (di-sodium salt), 2-methoxyethyl, 4-methoxybutyl,

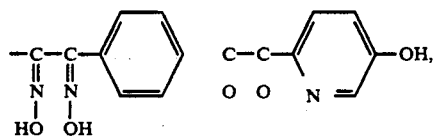

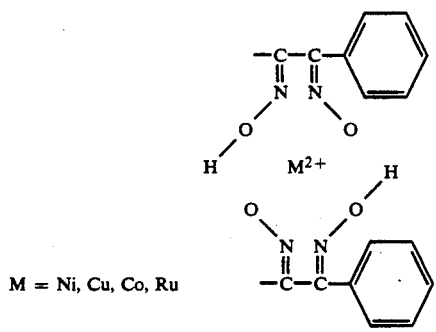

M = Ni, Cu, Co, Ru

A = A₁ = CH=N—R³   R³ = methyl, butyl, phenyl, p-nitrophenyl, p-dimethylaminophenyl The here mentioned examples should be only illustrative and not restrictive for this invention.

Examples of compounds with n=1 and
A=A₂=—CH=N-Z-N=CH—:

z=(single) bond, 1,2-ethanediyl, 1,4-butandiyl, 1,12-dodecanediyl, 1,4-phenyldiyl, 1,3-phenyldiyl, 1,4-naphthalenediyl, 1,5-naphthalenediyl, 1,8-naphthalenediyl, 1,4-(2-nitrophenyl)diyl, 3,5-(1,2,4-triazole)diyl, 2,7-fluorenediyl, 1,4-anthraquinonediyl, 1,5-anthraquinonediyl, 2,6-anthraquinoediyl, 2,6-(4-phenyl-1,3,5-triazine)diyl, 3,6-acridinediyl, 2,6-pyridinediyl, 3,7-(5-phenothiazinium)diylchlorid, 3,8-(5-ethyl-6-phenyl-phenanthridium)diylbromid,

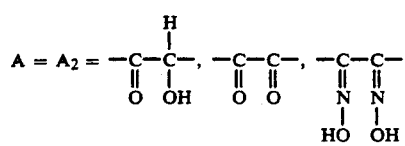

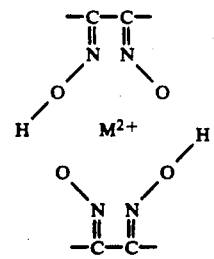

M = Ni, Cu, Co, Ru

The here mentioned example should be only illustrative and not restrictive for this invention.

EXAMPLE 1

2-(2',2'-dicyanovinyl)-5-acetoxymethyl-furan 1,68 g (10 mmol) 5-acetoxymethylfurfuraldehyde and 0,66 g (10 mmol) malononitrile are dissolved in 50 ml acetonitrile and with 40 mg β-alanine and 10 drops acetic acid are boiled at reflux for 10 h. When cooling the solution, the catalyst precipitates and is filtered off. After concentration one get 2,2 g of lilac-colored crystals with a melting point of 79° C. Recrystalization from methylene chloridea yields colorless crystals with m.p.=80°-82° C.

IR (KBr): 3130, 3100, 3040, 2990, 2940, 2230, 1750, 1610, 1565, 1225, 1195, 1005, 830 cm⁻¹

¹H-NMR(CDCl₃): 7.48 ppm (s), 7.34 ppm (d, 3.7 Hz), 6.67 ppm (d, 3.7 Hz), 5.15 ppm (s), 2.13 ppm (s)

EXAMPLE 2

Bis-5,5'(2'',2''-dicyanovinyl)-furfuraldehyde-azine 12,4 g (50 mmol) HMF-azine are dissolved in 500 ml 1,1,2-trichloroethane with heating and after addition of 115,3 g bariummanganate are boiled at reflux for 7 h. Then the solution is filtered hot and slowly is cooled. Yellow, needle-shaped crystals are formed with m.p.=214° C.

IR (KBr): 3140, 3115, 2850, 1670, 1630, 1490, 1410, 1250, 1175, 980, 955, 825, 795 cm⁻¹

¹H-NMR(DMSO): 9.74 ppm (s,CHO), 8.71 ppm (s), 7.68 ppm (d, 3.7 Hz), 7.38 ppm (d, 3.7 Hz)

2,44 g (10 mmol) dialdehyde and 1,32 g (20 mmol) malononitrile are dissolved in 150 ml acetonitrile and after addition of 40 mg β-alanine and 100 mg acetic acid are heated at reflux for 4 h. By slow cooling crystals are formed, which are filtered off and rinsed with cold solvent.

m.p.: 238°-242° C.

IR (KBr): 3120, 3030, 2220, 1595, 1535, 1380, 1285, 1205, 1197, 1135, 1023, 935, 810, 787, 770 cm⁻¹

¹H-NMR(DMSO): 8.62 ppm, 8.55 ppm, 8.35 ppm, 7.65-7.25 ppm

¹³C-NMR(DMSO): Signals of the predominantly present rotamer
154.0 ppm, 150.8 ppm, 150.0 ppm, 143.7 ppm, 125.7 ppm, 120.4 ppm, 114.2 ppm, 112.9 ppm, 77.9 ppm.

EXAMPLE 3

Bis 5-((2',2'-dicyanovinyl)-furfuryl)-ether 4,70 g (20 mmol) bis (5-formyl-furfuryl)-ether are dissolved in 150 ml toluene and 2,64 g (40 mmol) malononitri-le are added. Together with 50 mg β-alanine and 200 mg acetic acid the mixture is boiled at reflux for 4 h and is slowly cooled. The solids formed are filtered off and washed with toluene. Yield 5,40 g, m.p.: 148° C. (from toluene)

IR (KBr): 3130, 3045, 2920, 2224, 2212, 1608, 1548, 1494, 1340, 1211, 1194, 1140, 1123, 1029, 974, 798 cm$^{-1}$

NMR (DMSO): 8.26 ppm (s), 7.42 ppm (d, 3.65 Hz), 6.87 ppm (d, 3.65 Hz), 4.71 ppm (s)

EXAMPLE 4

Reaction of 2,2'-(2,5-furandiyldimethylidyne)bis-propanedinitrile with 8-methoxyheptafulvene (1:1) in dichloromethane.

To a fresh prepared, $N_2$- saturated solution of 650 mg (4.45 mmol) 8-methoxyheptafulvene in 30 ml absolute dichloromethane are added 980 mg (4.80 mmol) 2,2'-(2,5-furandiyldimethylidyne)bis-propandinitrile and about 10 mg hydroquinon and the mixture is stirred at room temperature for 18 h, excluding air with a mercury valve. The progress of the reaction is monitored by thin layer chromatography. After the cycloadducts had be formed, the formerly deep red solution turns transparent brown. The solvent is evaporated, the remaining brown oil dissolved in ether, filtered, the solvent in vacuo evaporated and the residue is dried in high vacuum. One gets a brownish solid.

By columne chromatography over silica gel with dichloromethane/petrol ether 2:1 as eluent, one obtains an orange solid with m.p. 172°-173° C. in a 52% yield.

MS(70 eV): m/e=322(100%, M+), 295 (31%, M-HCN)

IR(KBR) 3120, 3050, 2240, 1605, 1573, 1475, 1280, 1045, 820, 710 cm$^{-1}$

UV/VIS(CH$_3$CN): $\lambda_{max}$.(lg$\epsilon$)=250 (4.4), 327 (3.7), 443 nm (4.6)

$^1$H-NMR(250 MHz,CDCl$_3$): $\delta$=3.81 (m;1 H,H-8a),5.81 (dd,J=362

10.4 Hz,3.8 Hz;1 H,H-8), 6.32–6.38 (m;1 H,-H-7), 6.52–6.65 (m;3 H,H-4,H-5 H-6), 7.09 (d,J=4.0 Hz;1 H,furan-H), 7.12

(s;1 H,H-3), 7.30 (d,J=4.0 Hz; 1 H,-furan-H), 365 7.46 ppm(s;1 H,propanedinitril-H)

EXAMPLE 5

Reaction of 2,2'-(2,5-furandiyldimethylidyne)bis-propanedinitrile with 8-methoxyheptafulvene (1:2) in dichloromethane.

To a fresh prepared, $N_2$- saturated solution of 1.80 g (13 mmol) 8-methoxyheptafulvene in 100 ml absolute dichloromethane are added 850 mg (3.86 mmol) 2,2'(2,5-furandiyldimethylidyne) bis-propanedinitrile and ca. 10 mg hydroquinone and the mixture is stirred at room temperature for 1 day excluding air with a mercury valve. The progress of the reaction is monitored by thin layer chromatography. After termination of the cycloaddition the formerly deep red solution turns to transparent brown. The solvent is evaporated, the remaining brown oil is dissolved in ether, filtered, the solvent in vacua evaporated and the residue is dried in high vacuo. A brownish solid is obtained.

Methanol elimination from the formed tetrahydroazulene.

To a vigourously stirred solution of the formed tetrahydroazulene in 150 ml absolute benzene 20 g $P_2O_5$ and 2.8 g potassiumcarbonate are added and the solution is boiled at reflux for 6 h. After termination of the reaction the mixture is filtered through a Büchner fun-nel filled with sand and silica gel. The filtrate is concentrated in vacuo to a yellow-brown oil.

Via chromatography on silica gel with dichloromethane/petrolether (1:1) an orange solid is obtained in a 44% yield and with m.p.: 182°-184° C.

MS(70 eV): m/e 424(100%,M+), 397(11%,M-HCN), 370(11%,M-2 HCN)

IR(KBr): 1040, 780, 760, 698 cm$^{-1}$

UV/VIS(CH$_3$CN): $\lambda_{max}$.(lg$\epsilon$)=218(4.2), 245(4.2), 294(3.8), 354(4.0,s), 433,6(4.5), 456 nm(4.4)

$^1$H-NMR(250 MHz,CDCl$_3$): $\delta$=3.78(m,2 H,H-8a,H-8a'), 5.83(dd,

J=10.2 Hz,3.8 Hz;2 H,H-8,H-8'), 6.29–6.37 (m;2 H,H-7,H-7'), 6.40(d,J=6.0 Hz;2 H, H-4,H-4'), 6.46–6.83(m;4 H,H-6,H-6', H-5,H-5'), 6.86(s;2 H,H-3,H-3'), 7.02 (s;2 H,furan-H)

EXAMPLE 6

The electro-optical behavior of 2,2'-(2,5-furandiyldimethylidyne)bis-propanedinitrile.

Figure 1B:
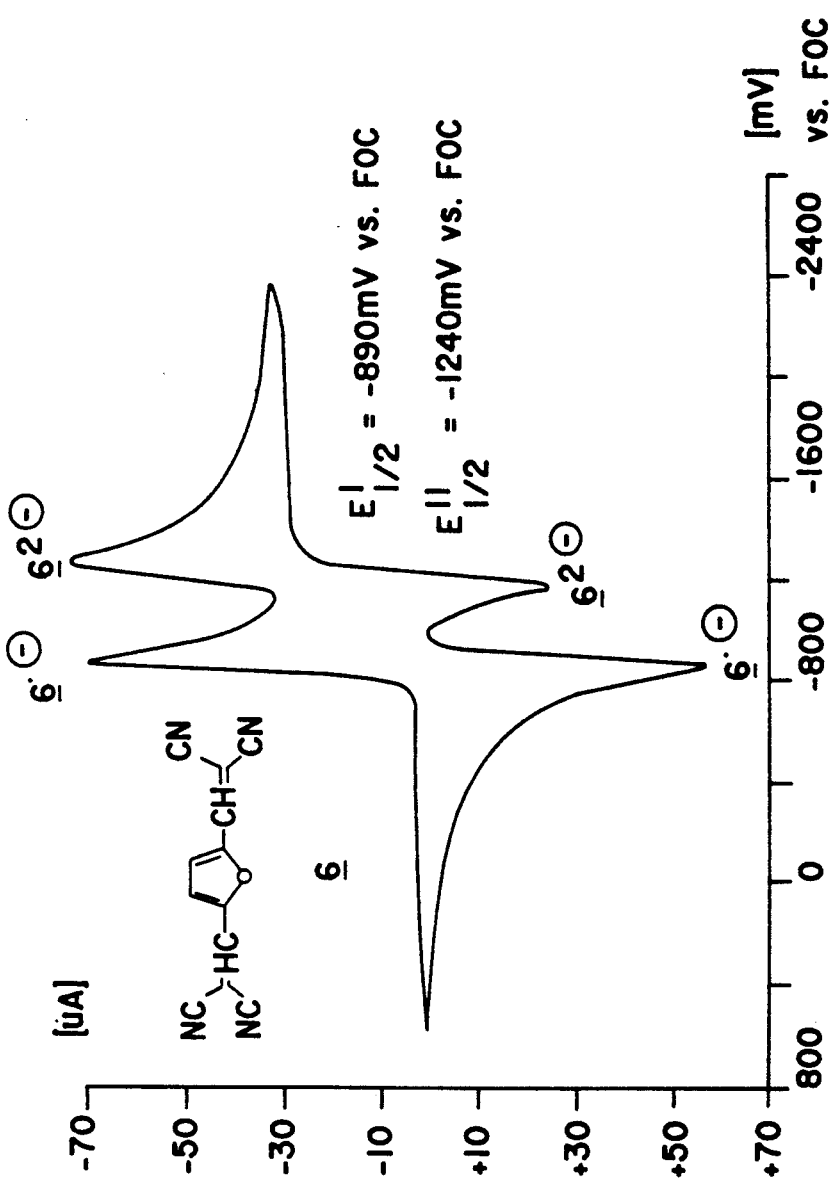

The reduction of 2,2'-(2,5-furandiyldimethylidyne)-bis-propanedinitrile (comuound 6) yields a radical anion and then a dianion 6$^{2-}$, which is, in contrast to the terephtal-derivative 7, fully reversible transformed to the neutral compound. This is shown in FIGS. 1A and 1B (cyclic voltammetry in acetonitrile 0.1 N tetrabutylammonium hexafluorophosphate).

Figure 2A:
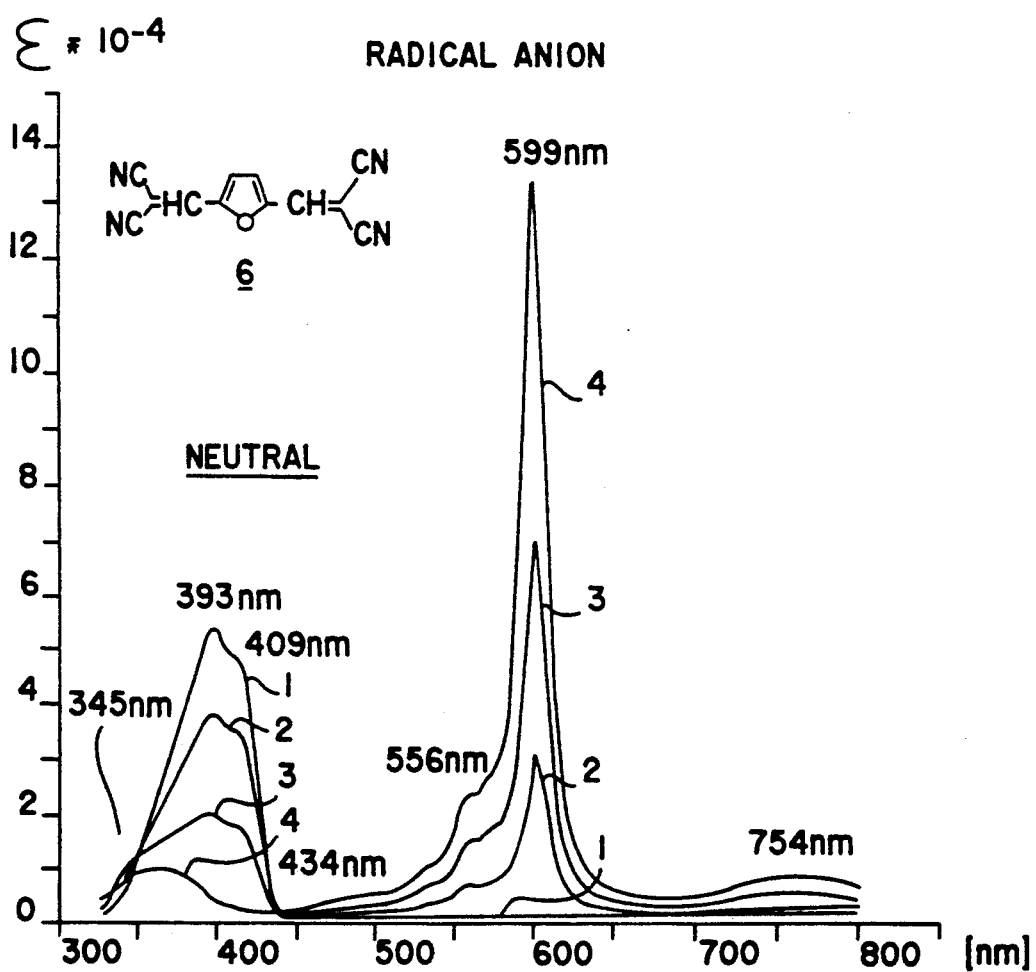
FIGS 2A and 2B are graphs of the optical absorption of 2,2'-(2,5-furandiyldimethylidyne)-bis-propanedinitrile, and reduction products thereof, in acetontrile and 0.1N tetrabutylammonium hexafluorophosphate, respectively.
Figure 2B:
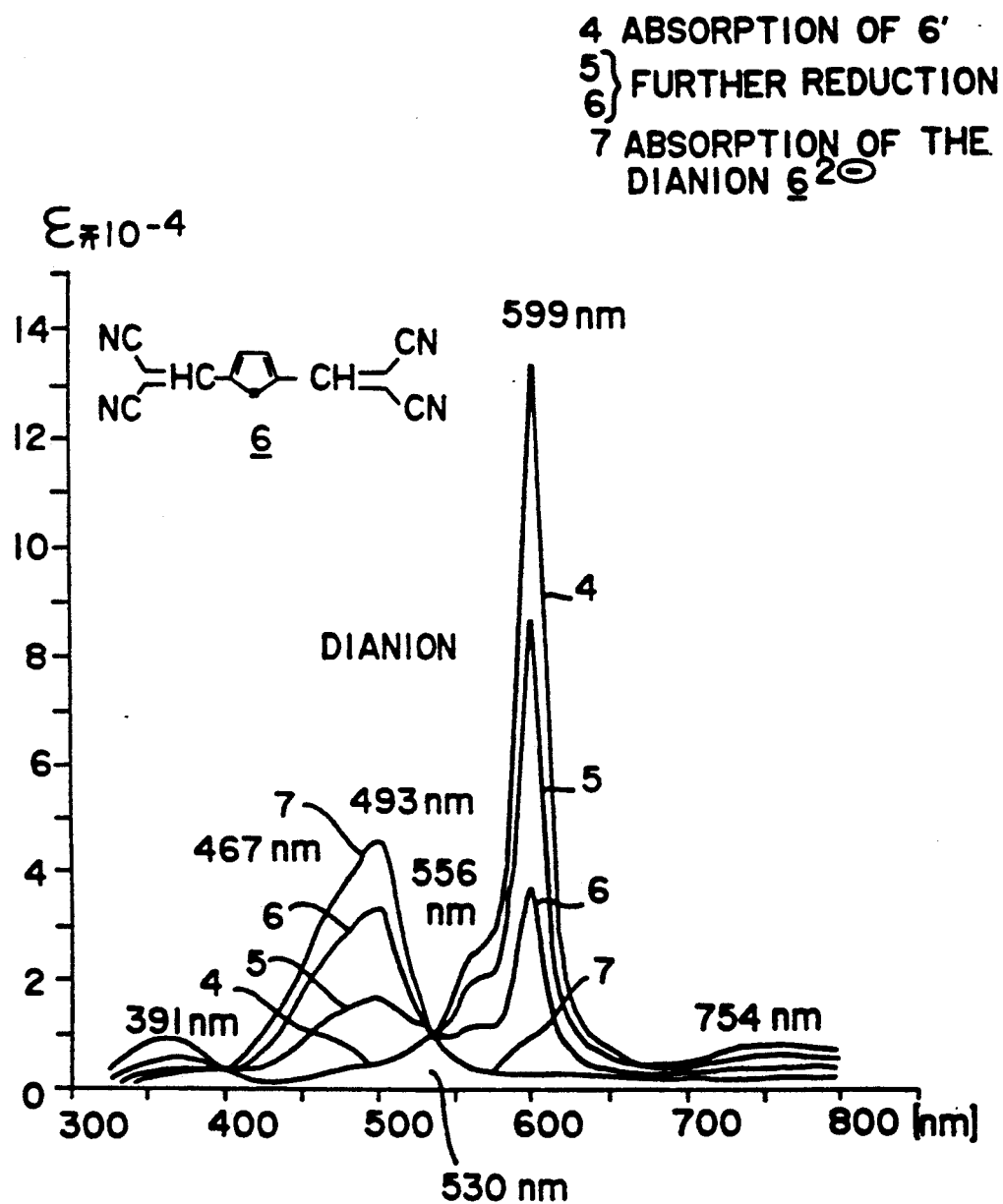

The optical properties of 6, the radical anion 6$\cdot^-$ and the dianion 6$^{2-}$ are shown in FIGS. 2A and 2B. The neutral compound 6 has a light-yellow color, according to an absorption at 393 nm (absorption 1), the radical anion 6$\cdot^-$ is deep blue, and the exceptionally narrow absorption at 599 nm is shown as curve 4 in FIG. 2A.

Further reduction yields the dianion 6$^{2-}$, which has an orange color (absorption maximum at 493 nm, in FIG. 2B. The conditions of the reduction are as follows: acetonitrile, 0.1N tetrabutylammonium hexafluorophosphate reduction to 6$\cdot^-$ at -1000 mV vs. ferrocene, reduction to 6$^{2-}$ at -1500 mV vs. ferrocene.

We claim:

1. A cycloadduct of the formula

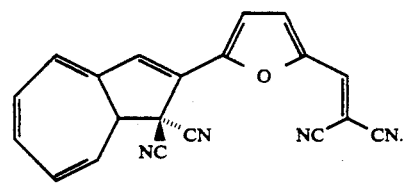

2. A process for preparing a cycloadduct of the formula

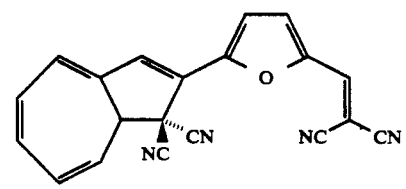

which comprises reacting 2,2'-(2,5-furandiyldimethylidyne)bis-propanedinitrile with 8-methoxyheptafulvene in the absence of air to form a tetrahydrozulene, and heating a solution of the tetrahydroazulene in a boiling solvent to eliminate methanol.

* * * * *